United States Patent [19]

Auer

[11] Patent Number: 4,510,438
[45] Date of Patent: Apr. 9, 1985

[54] COINCIDENCE CORRECTION IN PARTICLE ANALYSIS SYSTEM

[75] Inventor: Robert Auer, Miami, Fla.

[73] Assignee: Coulter Electronics, Inc., Ill.

[21] Appl. No.: 348,822

[22] Filed: Feb. 16, 1982

[51] Int. Cl.³ ............................................. G01N 27/00
[52] U.S. Cl. ................................... 324/71.4; 356/72; 377/12
[58] Field of Search .......................... 324/71.1, 71.4; 356/335–338, 72; 250/222.2; 377/11, 12; 364/555

[56] References Cited

U.S. PATENT DOCUMENTS

| | | | |
|---|---|---|---|
| 2,775,159 | 12/1956 | Frommer | 88/14 |
| 3,497,690 | 2/1970 | Wheeless et al. | 250/71 |
| 3,657,537 | 4/1972 | Wheeless et al. | 250/71 R |
| 3,710,933 | 1/1973 | Fulwyler et al. | 209/3 |
| 3,733,548 | 5/1973 | Coulter et al. | 324/71 CP |
| 3,786,261 | 1/1974 | Tucker | 250/205 |
| 3,893,766 | 7/1975 | Hogg | 356/36 |
| 3,910,702 | 10/1975 | Corll | 357/72 |
| 3,936,739 | 2/1976 | Hogg | 324/71 CP |
| 3,936,741 | 2/1976 | Coulter et al. | 324/71 CP |
| 3,938,038 | 2/1976 | Campbell | 324/71 CP |
| 3,940,691 | 2/1976 | Hogg | 324/71 CP |
| 3,949,197 | 4/1976 | Bader | 377/12 |
| 3,949,198 | 4/1976 | Coulter et al. | 235/92 PC |
| 3,968,429 | 7/1976 | Coulter et al. | 324/71 CP |
| 3,987,391 | 10/1976 | Hogg | 324/71 CP |
| 4,021,117 | 5/1977 | Göhde et al. | 364/555 |
| 4,140,395 | 2/1979 | Kreikebaum | 356/336 |
| 4,161,690 | 7/1979 | Feier | 324/71.4 |
| 4,298,836 | 11/1981 | Groves et al. | 324/71.1 |
| 4,348,107 | 9/1982 | Leif | 356/72 |

OTHER PUBLICATIONS

Thomas et al., "Combined Optical and Electronic Analysis of Cells with the AMAC Transducers", 1977, The Journal of Histochemistry and Cyto Chemistry, vol. 25, No. 7, pp. 827–835.
Leif et al., "Development of Instrumentation and Fluorochromes for Automated Multiparameter Analysis of Cells", 1977, Clinical Chemistry, vol. 23, No. 8, pp. 1492–1498.

Primary Examiner—Michael J. Tokar
Assistant Examiner—Kevin D. O'Shea
Attorney, Agent, or Firm—Silverman, Cass & Singer, Ltd.

[57] ABSTRACT

Flat beam optical sensing performed transverse of a flow aperture, of the particles passing through the aperture, directly indicates the presence of individual particles in the aperture. The indication can be used to eliminate or otherwise modulate the coincidence errors resulting in particle measurements taken through the length of the aperture.

29 Claims, 5 Drawing Figures

COINCIDENCE CORRECTION IN PARTICLE ANALYSIS SYSTEM

BACKGROUND OF THE INVENTION

This invention relates generally to electronic particle counting and analyzing apparatus utilizing an aperture and, in particular, relates to correcting errors in counting and analyzing resulting from the coincidence of a plurality of particles in the aperture.

Particle analysis apparatus using an aperture is well-known. See U.S. Pat. No. 2,656,508. The aperture of such apparatus provides a minute scanning aperture, ambit, or sensing zone relative to or through which pass and are detected, counted, and analyzed, single particles at a rate often well in excess of one thousand per second. Coincidence of two particles in the scanning ambit occurs quite often due to the physical parameters of the scanning aperture and particle concentration. The effect is that one particle is believed to be detected, counted and analyzed while two or more particles are actually located simultaneously in the sensing zone.

Correction for counting errors caused by such coincidence has been performed in several ways. One way is for an operator to refer to a coincidence correction chart which presents the proper error corrected count for a very large selection of counts produced by the device. This provides an accurate result but is time consuming and prohibits fully automatic recording and processing of error corrected counts.

Other ways have been developed which electrically manipulate the acutal count or the manner of obtaining the actual count to provide an error corrected count. U.S. Pat. No. 3,626,164 (U.S. Class 235/151.3) discloses circuitry which adds counts to the detected count to yield a corrected count which closely approximates the true particle count. U.S. Pat. No. 3,936,740 (U.S. Class 324/71 CP) discloses circuitry which digitally delays producing the pulses received from the Coulter aperture. U.S. Pat. No. 3,949,197 (U.S. Class 235/92 PC) discloses circuitry which provides a statistical correction to a detected train of particle derived count pulses so that the effective random coincidence loss or gain of the count does not induce ultimate counting error. And, U.S. Pat. No. 4,009,443 (U.S. Class 328/11) discloses circuitry which alters the time period in which particle pulses are counted. Other examples of coincidence correction in a Coulter aperture environment exist, but the stated examples are believed to be indicative of the cited U.S. classifications.

Thus, until the present invention, coincidence correction of a count of particles obtained in an aperture environment has been by operation on the electrical signals obtained from the aperture based upon some statistical theory. No attempt has been made directly to determine when this error causing coincidence exists.

In addition to counting errors, coincidence causes errors in analyzing other parameters, such as particle volume. When a particle passes through an aperture, its volume may be analyzed by the amount of change in electrical current flow through the aperture. Coincidence of two particles in the aperture causes a change in the flow of electrical current different from the change effected by either particle individually. This causes errors in particle volume determination which must be corrected for to determine the true particle volume. Again, no attempt previously has been made directly to determine when this error causing coincidence exists.

The present invention provides a method and apparatus for directly determining when a coincidence of particles in an aperture exists. The results of this direct determination may be used as desired, such as by correcting data containing coincidence errors, determining when valid data exists, or otherwise.

SUMMARY OF THE INVENTION

In accordance with the invention, a flat beam of radiant energy is passed through an aperture transverse of the direction of particle flow therethrough. Individual particles passing through the flat beam change the distribution of radiant energy exiting the flow chamber, which forms the aperture, sufficiently so that electrical detection signals may be produced in response thereto. The flat beam is dimensioned in the aperture so that the beam senses the entire cross section of the aperture and so that the beam senses the particles on a one-by-one basis.

Thereafter, the detection signals are used as desired to correct for coincidence errors in data obtained from the aperture by means other than the beam of radiant energy, such as in accordance with conventional aperture sensing principles. For example, a single detection signal during an electrical volume signal indicates no coincidence of particles in the aperture and a valid volume signal. More than one detection signal during a volume signal indicates coincidence of particles in the aperture and an erroneous volume signal.

In essence, the invention involves the optical sensing of a small domain, the cross section of the aperture, to indicate the validity of data obtained from a larger domain, the length of the aperture.

DESCRIPTION OF THE PREFERRED EMBODIMENT

Figure 1:
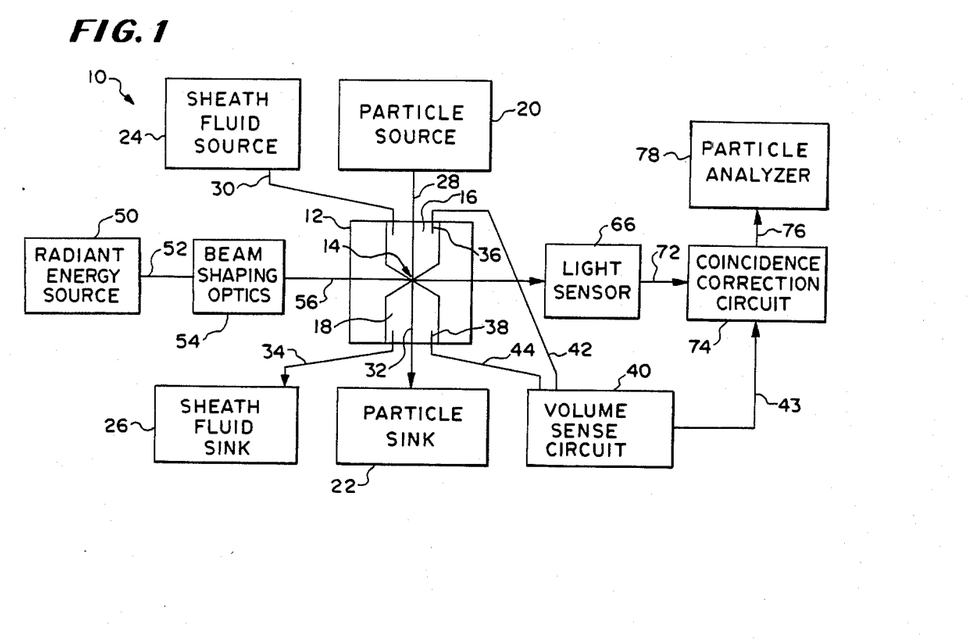
FIG. 1 is a schematic block diagram of a particle detection and analysis system utilizing an aperture, according to the invention.

Turning now to the drawing, in FIG. 1 an aperture particle analysis system is indicated generally by the reference character 10. This system, as is well-known, includes a flow chamber 12 providing an aperture 14 between an inlet chamber 16 and an outlet chamber 18. Particles to be analyzed are passed through the flow-chamber 12 and aperture 14 from a particle source 20 to particle sink 22. A sheath fluid source 24 and a sheath fluid sink 26 provide a sheath fluid also passing through the aperture 14 which aids in maintaining the particles from source 20 at the axial center of the aperture 14.

The sourcing and sinking of particles and sheath fluid to the flow chamber 12 may be of any means desired such as by tubing or other conduit. Thus, lead 28 indicates the means of carrying the particles from source 20 to the flow chamber 12. Lead 30 indicates the means carrying the sheath fluid from the source 24 to the flow chamber 12, lead 32 indicates the means carrying the particles from the flow chamber 12 to the particle sink 22 and lead 34 indicates the means carrying the sheath fluid from the flow chamber 12 to the sink 26.

The particle analysis system further includes a pair of electrodes 36 and 38 respectively located in the inlet chamber and outlet chamber of the flow chamber 12. The pair of electrodes are connected to a volume sense circuit 40 over leads 42 and 44 respectively. The volume sense circuit 40 provides a flow of electrical current through the length of aperture 14 by way of leads 42 and 44 and electrodes 36 and 38. As is well-known in a aperture particle analysis system, particles passing through the aperture 14 change the current flow through the aperture and this change in current can be measured in the volume sense circuit 40 to obtain an electrical signal indicative of the volume or other parameter of the particles passing through the aperture. The signals which are indicative of the volume of particles passing through the aperture are output on lead 42. The volume signal output on lead 42, however, includes coincidence errors which previously have been corrected for by various means as has been described hereinbefore.

In accordance with the invention, these coincidence errors are corrected for by passing a flat beam of radiant energy through the optically transparent walls of the flow-chamber 12 and, in particular, through the aperture 14, transverse of the direction of flow of particles therethrough. This beam of radiant energy is dimensioned so as to extend at least from wall to wall of the aperture and has a height in the direction of flow of particles which is about equal to the diameter of particles flowing through the aperture. When there are no particles passing through the beam of light in the aperture 14, the beam of radiant energy passes through the opposite wall of the flow chamber and exists therefrom to strike a beam stop. Radiant energy from the beam which is dispersed or scattered such as by being deflected or defracted therefrom due to imperfections in the flow-chamber walls or sheath fluid, also exists from the flow chamber body, is angled beyond the extent of the beam stop and strikes the face of an optical sensor. The optical sensor, in turn, provides a detection signal indicative of the amount of radiant energy striking its face.

When no particles are passing through the aperture 14 and the flat beam of radiant energy, the detection signal has a DC value, i.e., there is no change in its value. When a particle passes through the aperture 14 and the flat beam of radiant energy, it changes the distribution of radiant energy striking the face of the optical sensor due to the particle defracting and deflecting light from the flat beam. This change in distribution of radiant energy striking the face of the sensor causes a change in the value of the detection signal such that the detection signal produces a pulse or an AC value.

The pulse of the detection signal is used to indicate when individual particles are present at the location of the flat beam in the aperture 14. Because of the dimensions of the flat beam in the aperture 14, each pulse of the detection signal indicates the presence of a single particle in the aperture. Thus, multiple pulses of the detection signal occurring during a single volume signal on lead 42 indicates an erroneous volume value due to coincidence. Thereafter, the erroneous volume signal may be used as desired such as being disregarded, to avoid coincidence errors in the summation of particle volume signals obtained.

Figure 2:
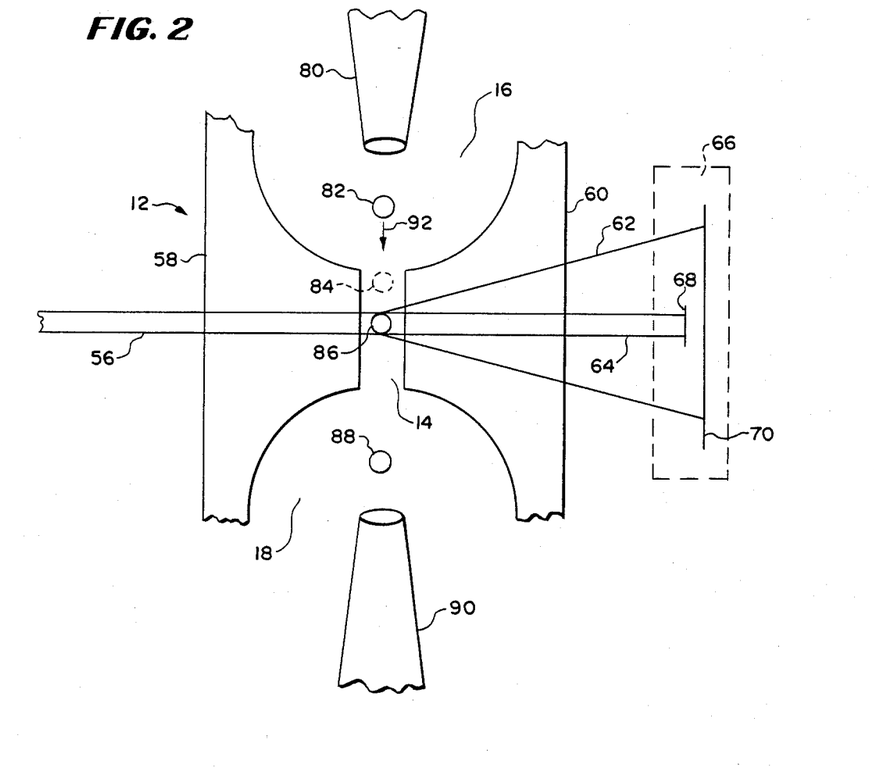
FIG. 2 is a side elevational view of a flow chamber in section along a median plane, including an aperture on an increased scale, illustrating a beam of radiant energy passing through said aperture transverse of the flow of particles therethrough.
Figure 3:
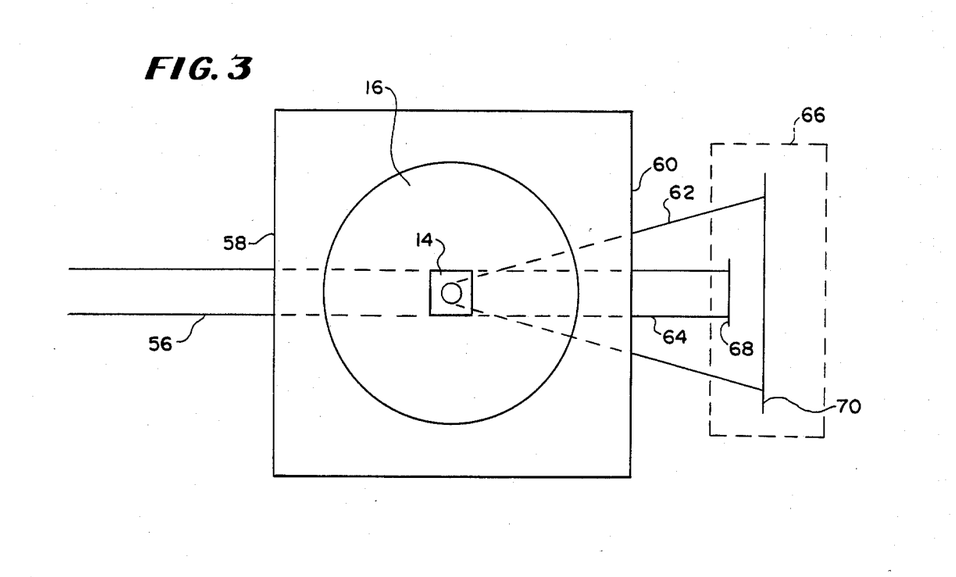
FIG. 3 is a top view of the flow chamber.

Turning again to FIG. 1, a radiant energy source 50 such as a laser provides a beam 52 of coherent radiant energy such as light. Thereafter, the beam 52 is passed through beam shaping optics 54 which shapes the beam 52 into a flat beam 56 having the desired dimensions as discussed. Thereafter, the flat beam 56 passes through the optically transparent walls 58 and 60 of flow chamber 12 and aperture 14. The radiant energy exiting the flow chamber 12 is shown in FIGS. 2 and 3 as being comprised of two portions, a first order beam which comprises light dispersed or scattered such as by defraction or deflection from flat beam 56, and the remainder of the radiant energy from flat beam 56 which forms a zero order beam 65. This zero order beam, of course, is formed of the radiant energy of flat beam 56, which is not dispersed or scattered therefrom. The radiant energy exiting the flow chamber 12 is directed onto a light sensor 66 (FIG. 1), which, as shown in FIG. 2, includes a zero order beam stop 68 and a face 70. The zero order beam is directed onto the beam stop 68 and is completely absorbed thereby. The first order beam substantially is directed onto the face 70 of the light sensor 66 and it is this energy which is used to provide the detection signal on lead 72, which is passed to a coincidence correction circuit 74. The output of the coincidence correction circuit on lead 76 thereafter is provided to a particle analyzer 78.

In FIG. 2 there is illustrated a diagrammatic representation of the flow chamber 12. Hatching of the walls 58 and 60 of the flow chamber 12 is omitted for clarity of the drawing. A source tube 80 provides particles such as 82, 84, 86 and 88 to the inlet chamber 16, aperture 14 and outlet chamber 18 and then through the tube 90 in a direction indicated by arrow 92. A sheath fluid from source 24 is also provided into inlet chamber 16, which passes through aperture 14 and into outlet chamber 18 and then to sink 26. Thus, inlet chamber 16 is in fluid communication with outlet chamber 18 through aperture 14, with the sheath fluid aiding in maintaining the particles in the axial center of aperture 14 to obtain a better volume signal therefrom.

For both mechanical and operational reasons, the aperture is many times longer than the diameter of the particles to be measured. Thus, there is a potential for multiple particles to be present in the aperture 14 at any one time and this is known as coincidence. An example of coincidence is indicated by the particles 84 and 86 being within the aperture 14 simultaneously.

As is illustrated in FIG. 2, the flat beam 56 has a thickness along the direction of the flow of the particles indicated by arrow 92, which is approximately equal to the diameter of the particles. In FIG. 3, it is shown that the beam 56 has a width which is substantially equal to the width of the aperture 14, i.e., the beam 56 extends substantially from wall to wall of the aperture 14. This is so that no particles in aperture 14 will escape detection.

In FIG. 3 a square aperture 14 is illustrated. It will be understood that the present invention is applicable also to an aperture of a round cross-section as will be discussed hereinafter.

Because the flat beam 56 is dimensioned to have a height approximately equal to the diameter of an individual particle, the individual particles passing through the aperture 14, are sensed on a one-by-one basis, even if the particles are closely spaced one from another. Thus, the flat beam 56 and light sensor 66 provide means by which the particles passing through the aperture 14 may be sensed on a one-by-one basis, separate from the determination of their volume and other than through the length of aperture 14.

Figure 5:
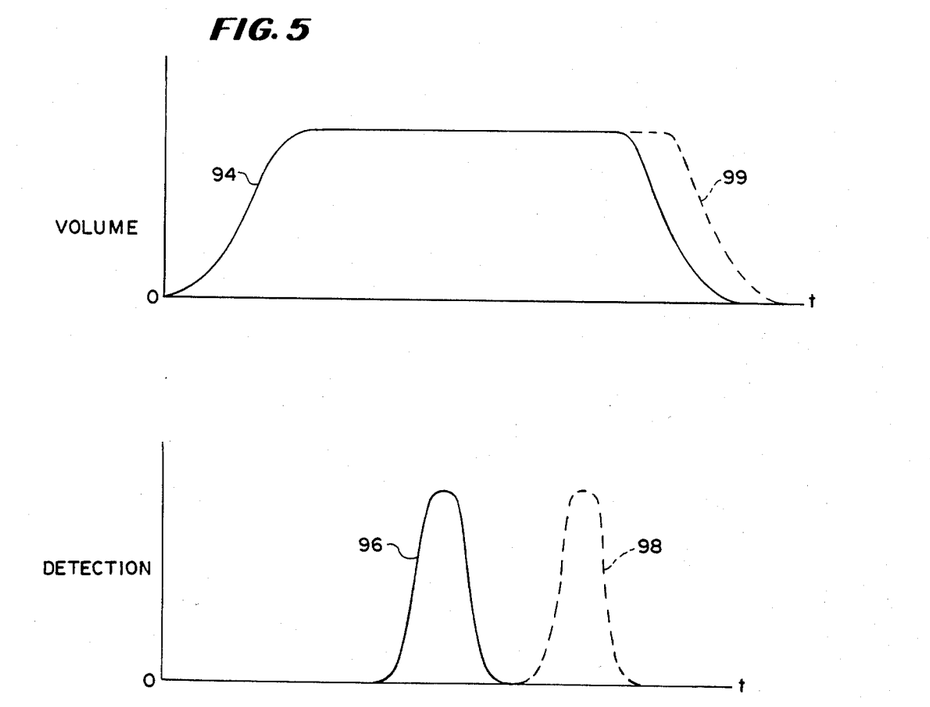
FIG. 5 is a graph illustrating the time relationship of detection signals and a volume signal produced in response to two particles passing through the aperture in coincidence.

In FIG. 5, the top graph, wave form 94 illustrates the volume signal obtained from circuit 40. The lower graph indicates the pulses of the detection signal output by the light sensor 66. The first pulse indicated by wave form 96 corresponds to particle 86 of FIG. 2 passing through the light beam 56, while the pulse represented by wave form 98 represents the pulse later produced by particle 84 passing through beam 56. The relative values of the wave forms 94, 96 and 98 are not intended to be represented accurately in FIG. 5, only the timing relationships between the occurrence of these signals. Thus, the occurrence of two pulses of the detection signal during one occurrence of the volume signal may be used to indicate a coincidence of particles in the aperture 14, while an occurrence of only one detection signal such as is represented by a wave form 96 indicates the presence of a signal particle in the aperture 14. This latter cause would occur if particle 84 of FIG. 2 were not in aperture 14 in coincidence with particle 86, and therefore, wave form 98 would not be produced during the occurrence of volume-signal wave form 94. Dashed-line wave form 99 illustrates the extension of the volume signal when particles 84 and 86 are in coincidence in the aperture.

Figure 4:
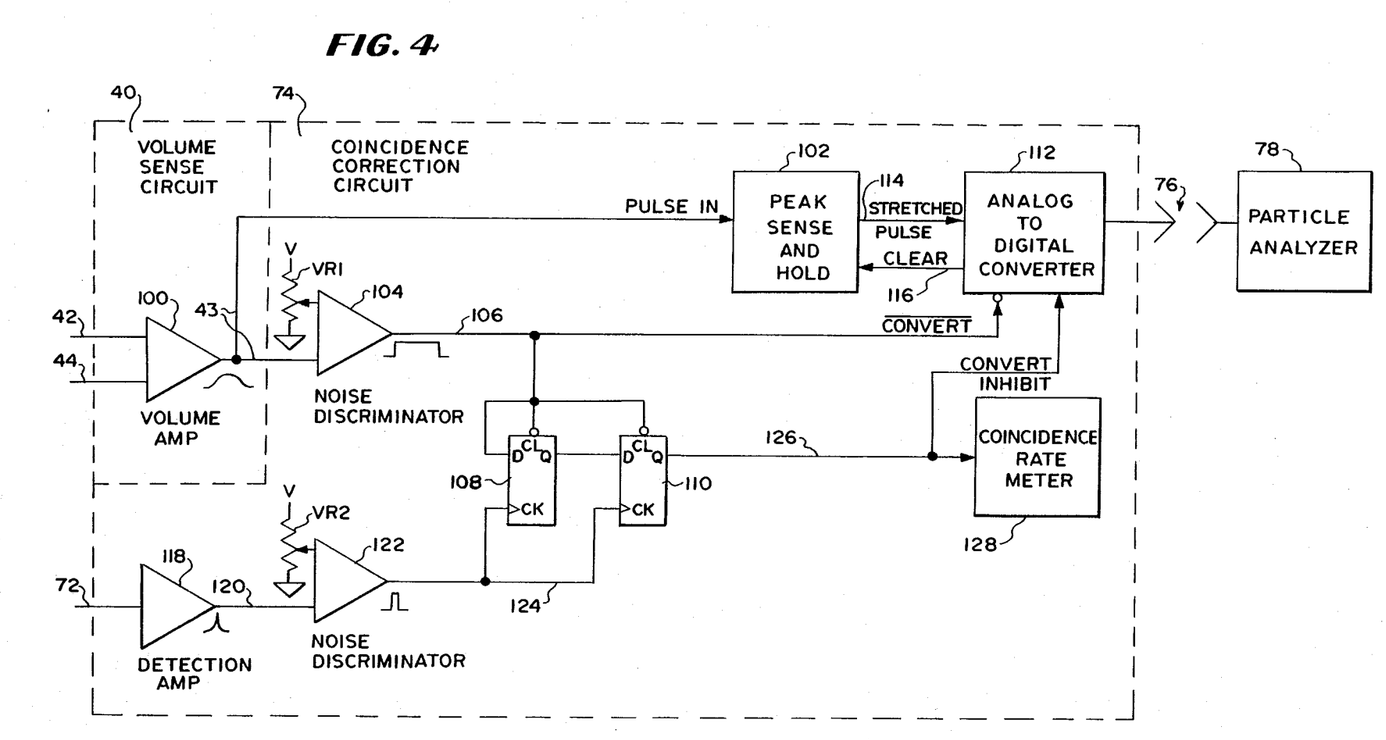
FIG. 4 is a circuit diagram illustrating a circuit which may be used with the invention to correct data for coincidence errors.

In FIG. 4, there is illustrated an embodiment of an electrical circuit used to modulate the coincidence including raw data from the volume sense circuit 40 to obtain corrected data free of said coincidence errors. Effectively, this circuit uses the pulses of the detection circuit to gate the passing of valid volume data to the analyzer 78.

The leads 42 and 44 from electrodes 46 and 48 are diagrammatically illustrated as bein input to volume amplifier 100. The output of volume amplifier 100 is essentially the output of volume circuit 40 on lead 42. This is a smooth wave form, substantially as illustrated by wave form 94 in FIG. 5. This signal is provided in coincidence correction circuit 74 to both a peak sense and hold circuit 102 and an input of a comparator 104 configured as a noise discriminator. The other input of the comparator 104 is connected to a variable resistance VR1 providing a noise threshold level voltage.

When the signal on lead 42 exceeds the noise threshold value selected by the variable resistor, comparator 104 outputs a corresponding signal on lead 106 which, hereafter will be known as $\overline{\text{CONVERT}}$, is applied to two D-type flip-flops 108 and 110 and analog to digital converter 112. The output of analog to digital converter 112 appears on lead 76 and analog to digital converter 112 is connected to peak sense and hold circuit 102 by leads 114 and 116. Lead 114 provides a signal known as STRETCHED PULSE to the AD converter 112 while lead 116 provides a CLEAR signal to the peak sense and hold circuit 102.

Also input to coincidence correction circuit 74 is a smooth wave signal from the sensor 66 on lead 72. This is amplified in amplifier 118 and is passed along on lead 120 to comparator 122 also configured as a noise discriminator. The other input of comparator 122 is connected to a variable resistor VR2 which is used to provide a noise threshold level voltage. When the signal on lead 120 is above this noise threshold level comparator 122 provides a corresponding signal on its output at lead 124. The signals on lead 124 correspond to the wave forms illustrated in the detection graph of FIG. 5. These signals or pulses are provided to the clock inputs of flip-flops 108 and 110. The Q output of flip-flop 110 is provided on lead 126 to both the analog to digital converter 112 and to a coincidence rate meter 128.

In operation, the amplifiers 100 and 118 are used to provide logic signals having useful levels. Both of the volume and detection signals from amplifiers 100 and 118 respectively, are compared to threshold levels to discriminate against noise. The outputs of the discriminators, represented by comparators 104 and 122, are squared wave forms whose durations are the length of the pulses applied thereto. The output of the volume noise comparator 104 is used to enable two D-type flip-flops 108 and 110. Both are cleared when no pulse is present out of the volume discriminator. Therefore, the Q outputs of both flip-flops are at the logic zero "0" state. During a volume signal, a detection pulse from the amplifier 122 clocks the two flip-flops one time. When this occurs, the Q output of flip-flop 108 goes to a logic one "1" state, and the Q output of flip-flop 110 remains at the logic zero "0" state. If a second pulse occurs in the detection signal during the volume signal, then the Q output of flip-flop 110 on lead 126 also goes to a logic one "1" state. Simultaneous to the operation of the flip-flops, the volume signal has been peak sensed and held to obtain the volume of the particle. The trailing edge of the volume discriminator signal $\overline{\text{CONVERT}}$, indicates to the analog to digital converter 112 to convert the stretched pulse from the peak sense and hold circuit 102 to a digital value. If the signal CONVERT INHIBIT on lead 126 is high or a logic one "1" state, when the trailing edge of the signal $\overline{\text{CONVERT}}$ occurs, then the analog to digital converter 112 does not digitally convert the value and, in turn, the converter 112 produces the CLEAR signal on lead 116 to clear the signal held in peak sense and hold circuit 102. If the signal on lead 126 is low or a logic zero "0" state, when the trailing edge of $\overline{\text{CONVERT}}$ occurs, then the converter 112 converts the sensed and held value to a digital value, outputs the same and then provides the CLEAR signal on lead 116. The signal on lead 126 can also be applied to a coincidence rate meter 128 to obtain a summation of the number of coincidence occurrences.

Thus, the coincidence correction circuit 74 may be thought of as gating the volume signal to the analog to digital converter 112 only when one detection pulse occurs during its duration.

In one particular embodiment of the invention, the particles to be analyzed have a diameter of about 1 to 20 micrometers. The length of the aperture has a length along the direction of particle flow of about 76 micrometers, while the flat beam 56 has a height along the direction of flow of the particles of about 5 micrometers.

As has been stated, the sensor 66 includes a zero order beam stop and a sensor for the first order dispersion of light. Such a sensor may be the sensor disclosed in U.S. Pat. No. 4,038,556 to Auer. Alternatively, the sensor may sense the change in the energy of the zero order beam caused by a particle passing through the flat beam 56 while ignoring the dispersed light of the first order beam, to provide a detection signal.

In FIG. 3, a square aperture 14 is illustrated and has been indicated that a round aperture will also work. This is because the electrical detection signal provided in response to the particle passing through the flat beam 56 is a result of the change in distribution of energy exiting the flow chamber 12 and detected by the photosensor and is not a function of the absolute quantity of light striking the sensor. In effect, the pulses of the detection signal are a result of the change of distribution of light striking the sensor and, thus, steady state characteristics of the system such as the index of refraction of the sheath fluid, the optical clarity of the walls of the fluid chamber and the cross-sectional configuration of the aperture are essentially irrelevant.

Modifications and variations of the present invention are possible in light of the above teachings. It is, therefore, to be understood that within the scope of the appended claims, the invention may be practiced otherwise than as specifically described.

What is claimed is:

1. Apparatus for correcting coincidence error occurring in parametric data obtained from a particle analysis system producing parametric data from particles, the correction being effected substantially at the time that the coincidence error occurs in a parametric datum of said data, the parametric datum representing at least one particle analysis parameter and the error being introduced into the datum at the time of measurement and resulting from coincidence of at least two particles in the length of a measurement aperture as said particles pass through the aperture, the apparatus comprising:
   A. measurement means producing said parametric datum in response to a measurement made through the lenth of said aperture as at least one particle passes through the length of the aperture, said measurement means being incapable of distinguishing between coincidence and non-coincidence of particles in the aperture;
   B. detection means producing a detection signal in response to sensing the presence of an individual particle in said aperture, the detection means sensing the presence of individual particles other than through the length of said aperture; and
   C. correction means for modulating said parametric datum in response to said detection signal after the production of said parametric datum and said detection signal to obtain corrected parametric data free of said coincidence error.

2. Apparatus for correcting coincidence error occurring in parametric data obtained from a particle analysis system producing parametric data from particles, the system including measurement means producing a parametric datum of said parametric data in response to a measurement made through the length of an aperture as at least one particle passes through the length of the aperture, said measurement means being incapable of distinguishing between coincidence and non-coincidence of particles in the aperture, the correction being effected substantially at the time that the coincidence error occurs in a parametric datum of said data, the parametric datum representing at least one particle analysis parameter and the error being introduced into the datum at the time of measurement and resulting from coincidence of at least two particles in the length of said measurement aperture as said particles pass through the aperture, the apparatus comprising:
   A. detection means producing a detection signal in response to sensing the presence of an individual particle in said aperture, the detection means sensing the presence of individual particles other than through the length of said aperture; and
   B. correction means for modulating said parametric datum in response to said detection signal after the production of said parametric datum and said detection signal to obtain corrected parametric data free of said coincidence error.

3. The apparatus as claimed in claims 1 or 2 in which said particles pass through said aperture in a first direction axial of said aperture and said detection means include a beam of radiant energy passing through said aperture transverse to said first direction.

4. The apparatus as claimed in claim 3 in which said beam is flat and further is dimensioned so that all of said particles passing through said aperture must pass through said flat beam.

5. The apparatus as claimed in claim 4 in which said aperture has a certain width, said particles have at least about one diameter and said flat beam has a height in said first direction of about said at least about one diameter and a width equal to about said certain width.

6. The apparatus as claimed in claim 3 in which said detection means include optical sensor means receiving the radiant energy from said beam of radiant energy passing through said aperture, said optical sensor means for producing said detection signal in response to a change in the distribution of radiant energy so received effected by said particles passing through said beam of radiant energy.

7. The apparatus as claimed in claim 6 in which said particles passing through said beam effect a first order beam comprising radiant energy dispersed from said beam and a zero order beam comprising the remainder of the radiant energy of said beam, and said optical sensor means include a beam stop receiving substantially all of said zero order beam and a face receiving substantially all of said first order beam.

8. The apparatus as claimed in claim 6 in which said detection signal includes pulses produced in response to particles passing through said beam of radiant energy.

9. The apparatus as claimed in claims 1 or 2 in which said correction means include gating means for gating each datum of said parametric data in response to said detection signal to pass a corrected parametric datum free of said coincidence errors.

10. The apparatus as claimed in claim 9 in which said detection signal includes pulses representing individual sensed particles, and said correction circuit means include sense and hold means for sensing and holding the value of each parametric datum, and counting means for counting the number of detection signal pulses occurring during each parametric datum, said gating means for gating each parametric datum from said sense and hold means in response to the number of detection signal pulses which are counted by said counting means during the production of that parametric datum.

11. The apparatus as claimed in claim 10 in which said gating means pass each parametric datum from said sense and hold means in response to one detection signal pulse being counted during the production of that parametric datum.

12. A method for correcting coincidence error occurring in parametric data obtained from a particle analysis system producing parametric data from particles, the system producing a parametric datum of said parametric data in response to a measurement made through the length of an aperture as at least one particle passes through the length of the aperture, said producing said parametric datum being incapable of distinguishing between coincidence and non-coincidence of particles in the aperture, the correction being effected substantially at the time that the coincidence error occurs in a parametric datum of said data, the parametric datum representing at least one particle analysis parameter and the error being introduced into the datum at the time of measurement and resulting from coincidence of at least two particles in the length of said measurement aperture as said particles pass through the aperture, the apparatus comprising:
  A. detecting the presence of individual particles in said aperture other than through the length of said aperture,
  B. producing a detection signal in response to detecting the presence of an individual particle in said aperture, and
  C. modulating said parametric datum in response to said detection signal after the production of said parametric datum and said detection signal to obtain corrected parametric data free of said coincidence error.

13. A method of correcting coincidence error occurring in parametric data obtained from a particle analysis system producing parametric data from particles, the correction being effected substantially at the time that the coincidence error occurs in a parametric datum of said data, the parametric datum representing at least one particle analysis parameter and the error being introduced into the datum at the time of measurement and resulting from coincidence of at least two particles in the length of a measurement aperture as said particles pass through the aperture, the method comprising:
  A. producing said parametric datum in response to a measurement made through the length of said aperture as at least one particle passes through the length of the aperture, said producing said parametric datum being incapable of distinguishing between coincidence and non-coincidence of particles in the aperture;
  B. detecting the presence of individual particles in said aperture other than through the length of said aperture,
  C. producing a detection signal in response to detecting the presence of an individual particle in said aperture, and
  D. modulating said parametric datum in response to said detection signal after the production of said parametric datum and said detection signal to obtain corrected parametric data free of said coincidence error.

14. The method as claimed in claim 12 or 13 in which said particles pass through said aperture in a first direction axial of said aperture and detecting said particles includes passing a beam of radiant energy through said aperture transverse to said first direction.

15. The method as claimed in claim 14 in which passing a beam of radiant energy through said aperture includes dimensioning said beam to be flat and so that all of said particles passing through said aperture must pass through said beam.

16. The method as claimed in claim 15 in which said aperture has a certain width, said particles have at least about one diameter and dimensioning said beam includes providing it with a height in said first direction of about said at least about one diameter and a width equal to about said certain width.

17. The method as claimed in claim 14 in which detecting said particles includes optically sensing the radiant energy received from said beam of radiant energy passing through said aperture, said optically sensing includes producing said detection signal in response to a change in the distribution of radiant energy so received effected by said particles passing through said beam of radiant energy.

18. The method as claimed in claim 17 in which said particles passing through said beam effects a first order beam comprising radiant energy dispersed from said beam and a zero order beam comprising the remainder of the radiant energy of said beam, and said optically sensing includes providing a beam stop receiving substantially all of said zero order beam and a face receiving substantially all of said first order beam.

19. The method as claimed in claim 17 in which producing said detection signal includes producing pulses in response to particles passing through said beam of radiant energy.

20. The method as claimed in claims 12 or 13 in which modulating said parametric data includes gating each parametric datum in response to said detection signal to pass a correct parametric datum free of said coincidence errors.

21. The method as claimed in claim 20 in which said detection signal includes pulses representing individual sensed particles, and said modulating said parametric data includes sensing and holding the value of each parametric datum, and counting the number of detection signal pulses occurring during the production of each parametric datum, said gating including gating each sensed and held parametric datum in response to the number of detection signal pulses which are counted during the production of that parametric datum.

22. The apparatus as claimed in claim 10 in which said gating means pass each parametric datum from said sense and hold means in response to said counting means counting one detection signal pulse during the production of that parametric datum.

23. Apparatus for correcting coincidence errors occurring in parametric data representing at least one particle analysis parameter of a plurality of particles, and obtained from a particle analysis system, the errors being effected by coincidence of the particles in an aperture as said particles pass through the length thereof, the apparatus comprising:
  A. measurement means for producing said parametric data in response to measurements taken through the length of said aperture as particles pass therethrough, there being one parametric datum produced for at least one particle passing through said aperture;
  B. detection means producing a detection signal in response to the detection, other than through the length of said aperture, of the presence of individual particles in said aperture; and
  C. correction circuit means for modulating said parametric data in response to said detection signals, said correction circuit means including gating means for gating each datum of said parametric data in response to said detection signal to pass a corrected parametric datum free of said coincidence errors.

24. Apparatus for correcting coincidence errors occurring in parametric data representing at least one particle analysis parameter of a plurality of particles, and obtained from a measurement means of a particle analysis system, the measurement means producing said parametric data in response to measurements taken through the length of an aperture as the particles pass therethrough, the errors being effected by coincidence of particles in the aperture as said particles pass through the length thereof, the apparatus comprising:

A. detection means producing a detection signal in response to the detection, other than through the length of said aperture, of the presence of individual particles in said aperture; and B. correction circuit means for modulating said parametric data in response to said detection signals, said correction circuit means including gating means for gating each datum of said parametric data in response to said detection signal to pass a corrected parametric datum free of said coincidence errors.

25. A method of correcting coincidence errors occurring in parametric data representing at least one particle analysis parameter of a plurality of particles, and obtained from measurement means of a particle analysis system, the measurement means producing said parametric data in response to measurements taken through the length of the aperture as the particles pass therethrough, the errors being effected by coincidence of the particles in the aperture as said particles pass through the length thereof, the method comprising:

A. detecting, other than through the length of said aperture, the presence of individual particles in said aperture;

B. producing a detection signal for each particle so detected; and

C. modulating said parametric data in response to said the detection signals, said modulating including gating each parametric datum in response to said detection signal to pass a correct parametric datum free of said coincidence errors.

26. A method of correcting coincidence errors occurring in parametric data representing at least one particle analysis parameter of a plurality of particles, and obtained from a particle analysis system, the errors being effected by coincidence of the particles in an aperture as said particles pass through the length thereof, the method comprising:

A. producing said parametric data in response to measurements taken through the length of said aperture as particles pass therethrough, there being one parametric datum produced for at least one particle passing through said aperture;

B. detecting, other than through the length of said aperture, the presence of individual particles in said aperture;

C. producing a detection signal for each particle so detected; and

D. modulating said parametric data in response to said detection signals, said modulating including gating each parametric datum in response to said detection signal to pass a correct parametric datum free of said coincidence errors.

27. The apparatus as claimed in claims 23 or 24 in which said detection signal includes pulses representing individual sensed particles, and said correction circuit means include sense and hold means for sensing and holding the value of each parametric datum, and counting means for counting the number of detection signal pulses occurring during each parametric datum, said gating means for gating each parametric datum from said sense and hold means in response to the number of detection signal pulses which are counted by said counting means during the production of that parametric datum.

28. The apparatus as claimed in claim 27 in which said gating means pass each parametric datum from said sense and hold means in response to one detection signal pulse being counted during the production of that parametric datum.

29. The method as claimed in claims 25 or 26 in which said detection signal includes pulses representing individual sensed particles, and said modulating said parametric data includes sensing and holding the value of each parametric datum, and counting the number of detection signal pulses occurring during the production of each parametric datum, said gating including gating each sensed and held parametric datum in response to the number of detection signal pulses which are counted during the production of that parametric datum.

* * * * *

UNITED STATES PATENT AND TRADEMARK OFFICE
CERTIFICATE OF CORRECTION

PATENT NO. : 4,510,438
DATED : April 9, 1985
INVENTOR(S) : Robert Auer

It is certified that error appears in the above-identified patent and that said Letters Patent is hereby corrected as shown below:

On the title page assignee should read

--(73) Assignee: Coulter Corporation, Hialeah, Fla. --.

Column 3, line 26, "42" should be --43--.
Column 3, line 27, "42" should be --43--.
Column 4, line 3, " 42" should be --43--.
Column 5, line 45, "42" should be --43--.
Column 5, line 53, "42" should be --43--.
Column 7, line 36, "lenth" should be --length--.

Signed and Sealed this

Thirtieth Day of September 1986

[SEAL]

Attest:

DONALD J. QUIGG

Attesting Officer

Commissioner of Patents and Trademarks